United States Patent [19]

Ahmad et al.

[11] 4,322,399

[45] Mar. 30, 1982

[54] VAGINAL SUPPOSITORY

[75] Inventors: Nawaz Ahmad, Piscataway; Leonard Kaplan, East Brunswick; George Ziets, Flemington, all of N.J.

[73] Assignee: Ortho Pharmaceutical Corporation, Raritan, N.J.

[21] Appl. No.: 86,621

[22] Filed: Oct. 19, 1979

[51] Int. Cl.$^3$ .......................... A61K 9/00; A61K 31/09
[52] U.S. Cl. .......................................... 424/44; 424/80; 424/341; 424/DIG. 14; 424/DIG. 15
[58] Field of Search ................... 424/44, 80, DIG. 14, 424/DIG. 15, 341

[56] References Cited

U.S. PATENT DOCUMENTS

| 3,136,692 | 6/1964 | Bandelin | 424/80 X |
| 3,876,757 | 4/1975 | Scherm | 424/44 |
| 4,151,274 | 4/1979 | Schlueter et al. | 424/80 |

OTHER PUBLICATIONS

McCutcheon's Detergents & Emulsifiers, p. 111, 1973.

*Primary Examiner*—Leonard Schenkman
*Attorney, Agent, or Firm*—Benjamin F. Lambert

[57] ABSTRACT

A spermicidally active suppository comprising an alkylphenoxypolyethoxyethanol as the spermicide, a mixture of water-soluble polyethylene glycols as the suppository base, a mixture of an organic acid and an inorganic bicarbonate as the foaming agents and a mixture of an amphoteric surfactant and a water-soluble film-forming agent as the foam-stabilizing agent.

13 Claims, No Drawings

VAGINAL SUPPOSITORY

This invention relates to a vaginal composition useful as an agent for contraception. In particular the invention relates to a vaginal suppository useful for contraception purposes which comprises a spermicide, a suppository base, a foaming agent and a foam-stabilizing agent.

The use of spermicidal substances such as suppositories, effervescent tablets and foams for local contraception is well known in the art. U.S. Pat. No. 2,854,377 describes nontoxic pharmaceutical compositions which effervesce on contact with moisture. In the latter patent surface active materials are added to conventional mixtures used to produce carbon dioxide for the purpose of creating more stable foams with smaller bubbles. U.S. Pat. No. 3,062,715 describes a vaginal tablet comprising effervescent powder and rubber substances which effect a rapid decomposition of the tablets and hence a rapid dissolution of the tablet. German Pat. No. 893,997 describes vaginal ovulae consisting of a wax-type carrier and a spermicide. After melting, the carrier, together with the aqueous body fluids, forms a tenacious emulsion of the oil-in-water type. However, the spermicide is not distributed homogeneously in the emulsion. U.S. Pat. No. 3,876,757 relates to an improvement in a composition comprising a spermicide, a water-soluble polyethylene glycol which melts at body temperature and a mixture of substances which produce carbon dioxide with water and a foam stabilizer. However, this composition apparently does not produce a homogeneous mixture unless the specified ratio of ingredients is employed.

Foam aerosols consisting of readily-prepared foams are also known in the art. However, foams of this type are difficult to handle. Dosing and introduction tubes are required for application of the foam, and if too little foam is used, the protective effect is correspondingly diminished.

The known means of local contraception, therefore, are not entirely satisfactory. There is a need for a contraceptive agent which can be easily introduced into the vagina and which will safely provide a sufficient amount of the spermicide at all times, even when the volume of the natural body fluids present in the vagina is low.

The present invention relates to a contraceptive composition comprising a spermicide, a foaming agent, a foam-stabilizing agent and a water-soluble suppository base. Contraception is achieved by a diffusion of the spermicide throughout the vaginal cavity due to the foaming action which occurs as a result of direct contact between the suppository and the vaginal fluid. The foaming suppository of the present invention rapidly develops its full effectiveness in a matter of minutes after application and maintains its effectiveness over a long period of time. The unique combination of ingredients results in a homogeneous composition which is capable of distributing the spermicide throughout the vaginal cavity.

According to the present invention, a mixture of water-soluble polyethylene glycols is employed as the suppository base. The mixture comprises a polyethylene glycol having a molecular weight of between about 1000 and 1200 and a second polyethylene glycol having a molecular weight of between about 1300 and 1600. The preferred mixture is a polyethylene glycol having a molecular weight of about 1000 and a polyethylene glycol having a molecular weight of about 1540. The mixture of glycols is present in a ratio of about 75–80% for the lower molecular weight polymer and about 3–5% for the higher molecular weight polymer.

As the foaming agent it is preferred to use a mixture of a water-soluble organic acid such as citric acid, tartaric acid and succinic acid and an alkaline or alkaline earth carbonate or bicarbonate such as sodium bicarbonate, sodium carbonate and potassium carbonate, for example. The preferred mixture is comprised of citric acid and sodium bicarbonate. The foaming agent is present in a ratio of from about 5–7%. The preferred ratio is about 2% of the acid component and about 4% of the basic salt. Although a lower ratio of the foaming agent is employed in the present invention than in the prior art suppositories, the foaming agent yields sufficient carbon dioxide development to effect a thorough diffusion of the spermicide in the vaginal cavity. Thus a smaller evolution of gas and a lower increase in temperature occur which results in fewer of the side effects generally associated with effervescent suppositories of this type. The mixture provides a system having a pH between about 4.5 and 7.5.

A mixture of foam-stabilizing agents is added to assure even development of the foam as well as uniformity and consistancy over an extended period of time. As the foam-stabilizing agent a mixture of an amphoteric organic surfactant and a water-soluble film-forming agent is employed. The organic surfactant serves as a foam stabilizer and in addition tends to reduce the irritation commonly associated with compositions of this type. The film-forming agent serves as a support or binding agent for the foam after it is produced. The film-forming agent also increases the viscosity of the fluid in the vaginal cavity resulting in an increased barrier effect for the suppository. Amphoteric surface-active agents which can be employed include Amphoteric-1, Amphoteric-2, Amphoteric-5, Amphoteric-6, Amphoteric-9, Amphoteric-10, Amphoteric-14, Amphoteric-19, and Amphoteric-20 (sold by Miranol Chemical Co., Inc.), Monateric CA, Monateric CSH-32, Monateric ISA-35, Monateric CM-36S, Monateric 805 and Monateric CAB (sold by Mona Industries, Inc.). The preferred surface-active agent is Amphoteric-19. Amphoteric-1 is a long chain imidazoline type of zwitterion which conforms generally to the formula

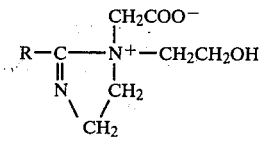

where R is derived from the coconut fatty radical. Amphoteric-2 is a long chain imidazoline type of zwitterion which conforms generally to the formula

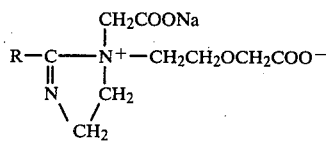

where R is derived from the coconut fatty radical. Amphoteric-5 is a long chain imidazoline type of zwitterion which is generally described as a sodium trideceth sulfate derivative of Amphoteric-2. Amphoteric-6 is a long chain imidazoline type of zwitterion which is generally described as a sodium lauryl sulfate derivative of Amphoteric-2. Amphoteric-9 is a long chain imidazoline type of zwitterion which conforms generally to the formula

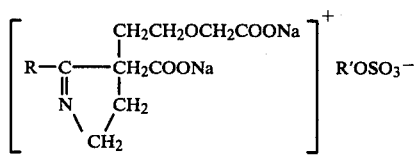

where R is derived from the coconut fatty radical and R' is derived from a mixture of lauryl and laureth-3 radicals. Amphoteric-10 is a long chain imidazoline type of zwitterion which conforms generally to the formula

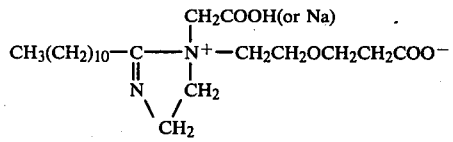

Amphoteric-14 is a long chain imidazoline type of zwitterion which conforms generally to the formula

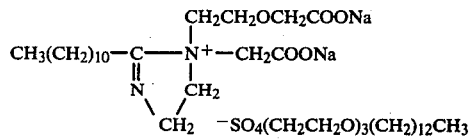

Amphoteric-19 is a long chain imidazoline type of zwitterion which conforms generally to the formula

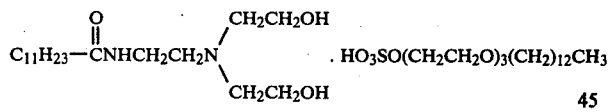

Amphoteric-20 is a long chain imidazoline type of zwitterion which conforms generally to the formula

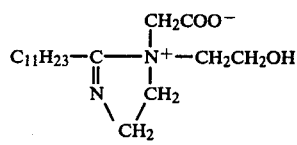

Monateric CA (Amphoteric-11) is the amphoteric organic compound that conforms generally to the formula

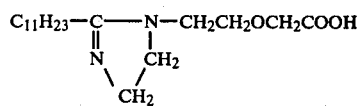

Monateric CSH-32 is a fully biodegradable amphoteric in the form of a 32% active sodium salt of a dicarboxymethyl fatty acid derived imidazoline.

Monateric ISA-35 (Amphoteric-12) is the amphoteric organic compound that conforms generally to the formula

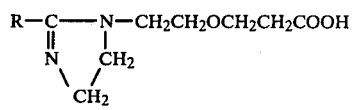

where R is derived from isostearic acid.

Monateric CM-36S is a coco-imidazoline based amphoteric.

Monateric 805 (Amphoteric-18) is the amphoteric organic compound that conforms generally to the formula

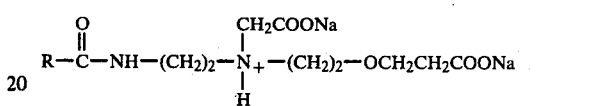

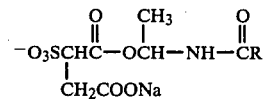

and Monateric CAB is a coco-amido betaine. As the film-forming agent Povidone K26-28 having a molecular weight of about 38,000, Povidone K29-32 having a molecular weight of about 39,450 (sold by General Aniline & Film Corp.), Cellulose gum, Hydroxyethylcellulose, Cellulose ether and Reten 205 a cationic water-soluble polymer (sold by Hercules Powder Co.), and sodium-alginate may be employed. The preferred film-forming agent is Povidone K29-32 (polyvinylpyrrolidone). The mixture of foaming stabilizing agents is employed in a ratio from about 4–10%. The preferred mixture is about 2% of the surface active agent and about 5% of the film-forming agent.

As the spermicide it is preferred to use an alkylphenoxyethoxyethanol of the formula

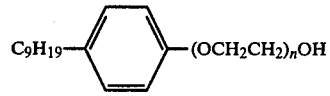

wherein n is an integer from 5–12. The preferred spermicide is a nonylphenoxypolyethoxyethanol wherein n is 9, commonly known as nonoxynol-9. The spermicide distributes itself homogeneously in the foam as it forms and the foam and spermicide are distributed equally and evenly over the entire vaginal cavity as the foam develops. The spermicide is present in a ratio of from about 2–7%. In a preferred embodiment about 5–6% of the spermacide is employed.

Although the contraceptive composition of the present invention may be prepared in a variety of shapes, it is preferred to use a torpedo-shaped suppository having a smooth surface appearance. The suppository has a weight between about 1.6 and 2 grams. The preferred weight is about 1.8 grams. The suppository is prepared by adding the spermicide to a heated mixture of the polyethylene glycols with stirring until a clear solution is obtained. The amphoteric surfactant is added to the clear solution followed by the addition of the organic acid. The film-forming agent is then added to the mixture and the mixing is continued until a uniform mixture is obtained. The alkali or alkaline earth metal carbonate is then added and the mixture is poured into the suppository shell and evolved until it solidifies. A more detailed description of the process according to the invention is described in Example I.

EXAMPLE I

A mixture of a polyethylene glycol having a molecular weight of about 1000 (1395 mg) and a polyethylene glycol having a molecular weight of about 1540 (71.0 mg) is heated at 52°–62° C. with constant mixing until a clear solution is obtained. Nonoxynol-9 (100 mg) is added and the stirring is continued. The temperature is adjusted to 52°–62° C. and Amphoteric-19 (36 mg) is added with stirring. The stirring is continued until a clear solution is obtained after which anhydrous citric acid (40.5 mg) is added with stirring. The stirring is continued until the citric acid dissolves after which Povidone K29-32 (90 mg) is added with stirring. The temperature of the mixture is adjusted to 52°–62° C. and the stirring is continued until a uniform suspension is formed. The mixture is cooled to 43°–47° C. after which sodium bicarbonate (47.5 mg) is added with stirring. The mixture is stirred at 43°–47° C. for 20 minutes after which it is poured into a suppository shell.

The suppository prepared by the above process has the following composition:

| Ingredient | Percent | wt. (grams) |
| --- | --- | --- |
| nonoxynol-9 | 5.56 | 0.1000 |
| Amphoteric-19 | 2.00 | 0.0360 |
| Povidone | 5.0 | 0.0900 |
| citric acid, anhydrous | 2.25 | 0.0405 |
| sodium bicarbonate | 3.75 | 0.0675 |
| polyethylene glycol 1000 | 77.50 | 1.3950 |
| polyethylene glycol 1540 | 3.94 | 0.0710 |
| | 100.00% | 1.8000 g |

The suppository dissolves completely in about 1 ml of water in about 10 minutes at a temperature of about 37° C. Upon contact with the water, a slight development of foam starts with simultaneous dissolution of the suppository. The foam development increases constantly until the dissolution is complete. The foam which forms shows fine pores, is even and remains as such over an extended period of time.

The above example is provided by way of illustration and is not intended to limit the scope of the present invention, the scope of which is defined by the appended claims.

What is claimed is:

1. A spermicidally active vaginal suppository comprising about 2–7% by weight of an alkylphenoxypolyethoxyethanol as the spermicide, about 75–85% of a mixture of water-soluble polyethylene glycols as the suppository base, about 5–7% of a mixture of an organic acid and an inorganic bicarbonate as the foaming agent and about 4–10% of a mixture of an amphoteric surfactant selected from the group consisting of Amphoteric-1, Amphoteric-2, Amphoteric-5, Amphoteric-6, Amphoteric-9, Amphoteric-10, Amphoteric-14, Amphoteric-19, Amphoteric-20, Monateric CA, Monateric CSH-32, Monateric ISA-35, Monateric CM-36S, Monateric 805 and Monateric CAB and a water-soluble film-forming agent selected from the group consisting of Povidone K26-28, Povidone K29-32, cellulose gum, hydroxyethylcellulose, cellulose ether, Reten 205 and sodium alginate as the foam-stabilizing agent.

2. A spermicidally active vaginal suppository according to claim 1 wherein the alkylphenoxypolyethoxyethanol is p-nonylphenoxypolyethoxyethanol.

3. A spermicidally active vaginal suppository according to claim 1 wherein the mixture of water-soluble polyethylene glycols consists of 75–80% of glycols having a molecular weight of between 1000 and 1200 and 3–5% of glycols having a molecular weight of between 1300 and 1600.

4. a spermicidally active vaginal suppository according to claim 3 wherein the mixture of water-soluble polyethylene glycols consists of 75–80% of glycols having a molecular weight of about 1000 and 3–5% of glycols having a molecular weight of about 1540.

5. A spermicidally active vaginal suppository according to claim 1 wherein the organic acid is selected from the group consisting of citric acid, tartaric acid and succinic acid and the inorganic bicarbonate is selected from the group consisting of sodium bicarbonate and potassium bicarbonate.

6. A spermicidally active vaginal suppository according to claim 5 wherein the organic acid is citric acid and the inorganic bicarbonate is sodium bicarbonate.

7. A spermicidally active vaginal suppository according to claim 1 wherein the amphoteric surfactant is Amphoteric-19 and the water-soluble film-forming agent is Povidone K29-32.

8. A spermicidally active vaginal suppository according to claim 1 comprising 5.5% by weight of an alkylphenoxypolyethoxyethanol as the spermicide, a mixture of 77.5% of a polyethylene glycol having a molecular weight of 1000 and 3.9% of a polyethylene glycol having a molecular weight of 1540 as the mixture of water-soluble polyethylene glycols, a mixture of 2.25% of an organic acid and 3.75% of an inorganic bicarbonate as the foaming agent and a mixture of 5% of a film-forming agent selected from the group consisting of Povidone K26-28, Povidone K29-32, cellulose gum, hydroxyethylcellulose, cellulose ether, Reten 205 and sodium alginate and 2% of an amphoteric surfactant selected from the group consisting of Amphoteric-1, Amphoteric-2, Amphoteric-5, Amphoteric-6, Amphoteric-9, Amphoteric-10, Amphoteric-14, Amphoteric-19, Amphoteric-20, Monateric CA, Monateric CSH-32, Monateric ISA-35, Monateric CM-36S, Monateric 805 and Monateric CAB as the foam stabilizer.

9. A spermicidally active vaginal suppository according to claim 8 wherein the alkylphenoxypolyethoxyethanol is p-nonylphenoxypolyethoxyethanol.

10. A spermicidally active vaginal suppository according to claim 8 wherein the organic acid is selected from the group consisting of citric acid, tartaric acid and succinic acid and the inorganic bicarbonate is selected from the group consisting of sodium bicarbonate and potassium bicarbonate.

11. A spermicidally active vaginal suppository according to claim 10 wherein the organic acid is citric acid and the inorganic bicarbonate is sodium bicarbonate.

12. A spermicidally active vaginal suppository according to claim 8 wherein the amphoteric surfactant is Amphoteric-19 and the film-forming agent is Povidone K29-32.

13. A spermicidally active vaginal suppository according to claims 1 or 8 having a torpedo-shaped form and a weight of between 1.60 and 2.0 grams.

* * * * *

UNITED STATES PATENT AND TRADEMARK OFFICE
CERTIFICATE OF CORRECTION

PATENT NO. : 4,322,399

DATED : March 30, 1982

INVENTOR(S) : Nawaz Ahmad et al.

It is certified that error appears in the above—identified patent and that said Letters Patent is hereby corrected as shown below:

Column 5, line 56, "75-85%" should be -- 78-85% -- .

Column 6, line 12, "a spermicidally" should be
-- A spermicidally --.

Signed and Sealed this

Seventh Day of September 1982

[SEAL]

Attest:

Attesting Officer

GERALD J. MOSSINGHOFF

Commissioner of Patents and Trademarks